(12) United States Patent
Nielsen

(10) Patent No.: US 7,070,580 B2
(45) Date of Patent: Jul. 4, 2006

(54) INFUSION DEVICE AND AN ADHESIVE SHEET MATERIAL AND A RELEASE LINER

(75) Inventor: Jens Egebjerg Nielsen, Ringsted (DK)

(73) Assignee: Unomedical A/S, Lynge (DK)

( * ) Notice: Subject to any disclaimer, the term of this patent is extended or adjusted under 35 U.S.C. 154(b) by 338 days.

(21) Appl. No.: 10/404,340

(22) Filed: Apr. 1, 2003

(65) Prior Publication Data
US 2004/0199123 A1   Oct. 7, 2004

(51) Int. Cl.
*A61M 5/32* (2006.01)
(52) U.S. Cl. ...................................... 604/180
(58) Field of Classification Search ............ 604/20–21, 604/48, 93.01, 174, 180; 128/DIG. 6; 424/447–449; 428/43
See application file for complete search history.

(56) References Cited

U.S. PATENT DOCUMENTS

| | | | |
|---|---|---|---|
| 643,544 A | 2/1900 | Simmons | |
| 1,838,825 A | 12/1931 | Goldstein | |
| 1,991,103 A | 2/1935 | King | |
| 2,047,010 A | 7/1936 | Dickinson | |
| 2,295,849 A | 9/1942 | Kayden | |
| 2,319,731 A | 5/1943 | Garrett | |
| 2,533,731 A | 12/1950 | Gomberg | |
| 2,630,803 A | 3/1953 | Baran | |
| 2,730,099 A | 1/1956 | Sullivan | |
| 2,952,420 A | 9/1960 | Von Hoorn | |
| 3,154,080 A | 10/1964 | Rowan et al. | |
| 3,610,240 A | 10/1971 | Harautuneian | |
| 3,783,996 A | 1/1974 | Gerard et al. | |
| 3,814,097 A | 6/1974 | Ganderton et al. | |
| 3,840,011 A | 10/1974 | Wright | |
| 3,870,220 A * | 3/1975 | Koury et al. | 229/401 |
| 3,942,528 A | 3/1976 | Loeser | |
| 4,014,328 A | 3/1977 | Cluff et al. | |
| 4,146,113 A | 3/1979 | Gavel | |
| 4,150,798 A | 4/1979 | Aragon | |
| 4,267,836 A | 5/1981 | Whitney et al. | |
| 4,306,705 A | 12/1981 | Svenson | |

(Continued)

FOREIGN PATENT DOCUMENTS

DE    196 31 921    3/1997

(Continued)

OTHER PUBLICATIONS

Search Report corresponding to International Application No. PCT/DK2004/000221, dated Jun. 28, 2004.

*Primary Examiner*—LoAn H. Thanh
(74) *Attorney, Agent, or Firm*—Brinks Hofer Gilson & Lione

(57) ABSTRACT

An infusion device (1) comprising a housing (3) with an upper face plate (4) and a lower face plate (5) and an adhesive sheet material (101) placed on the lower face plate (5) for securing the infusion device (1) to the skin, the adhesive sheet material (101) comprising a backing layer (102) which has an adhesive layer (103) on one surface, the adhesive layer (103) being covered by a removable release liner (104), and wherein the release liner (104) comprising at least one score line (106) comprising a spiral or helix, wherein the starting point (107) for the score line (106) is placed in the periphery (108) of the release liner (104) and wherein the score line (106) continues to an end point placed on the border of the periphery (110) of a central aperture (105) of the release liner.

12 Claims, 5 Drawing Sheets

U.S. PATENT DOCUMENTS

| | | |
|---|---|---|
| D267,199 S | 12/1982 | Koenig |
| 4,365,630 A | 12/1982 | McFlarlane |
| 4,406,042 A | 9/1983 | McPhee |
| 4,517,971 A | 5/1985 | Sorbonned |
| 4,530,695 A | 7/1985 | Phillips et al. |
| 4,531,686 A | 7/1985 | Shaw |
| 4,576,846 A | 3/1986 | Noel |
| 4,606,735 A | 8/1986 | Wilder et al. |
| 4,616,790 A | 10/1986 | Beltran |
| 4,637,404 A | 1/1987 | Gessman |
| 4,662,873 A | 5/1987 | Lash et al. |
| 4,682,702 A | 7/1987 | Gach |
| 4,713,059 A | 12/1987 | Bickelhaupt et al. |
| 4,734,092 A | 3/1988 | Millerd |
| 4,755,173 A | 7/1988 | Konopka et al. |
| 4,802,638 A | 2/1989 | Burger et al. |
| 4,817,603 A | 4/1989 | Turner et al. |
| RE32,922 E | 5/1989 | Levin et al. |
| 4,838,871 A | 6/1989 | Luther |
| 4,850,974 A | 7/1989 | Bickelhaupt et al. |
| 4,878,897 A | 11/1989 | Katzin |
| 4,895,570 A | 1/1990 | Larkin |
| D306,500 S | 3/1990 | Brahler |
| 4,913,369 A | 4/1990 | Lia et al. |
| 4,917,669 A | 4/1990 | Bonaldo |
| 4,978,338 A | 12/1990 | Melsky et al. |
| 4,982,842 A | 1/1991 | Hollister |
| 4,994,045 A | 2/1991 | Ranford |
| 5,011,475 A | 4/1991 | Olson |
| 5,098,389 A | 3/1992 | Cappucci |
| 5,112,313 A | 5/1992 | Sallee |
| 5,116,324 A | 5/1992 | Brierley et al. |
| 5,116,325 A | 5/1992 | Paterson |
| 5,121,751 A | 6/1992 | Panalletta |
| 5,141,496 A | 8/1992 | Dalto et al. |
| 5,147,319 A | 9/1992 | Ishikawa et al. |
| 5,147,375 A | 9/1992 | Sullivan et al. |
| 5,161,681 A | 11/1992 | Kemp et al. |
| 5,163,915 A | 11/1992 | Holleron |
| 5,176,662 A | 1/1993 | Bartholomew et al. |
| 5,188,314 A | 2/1993 | Peters |
| 5,188,611 A | 2/1993 | Orgain |
| RE34,223 E | 4/1993 | Bonaldo |
| 5,222,947 A | 6/1993 | D'Amico |
| 5,232,454 A | 8/1993 | Hollister |
| 5,236,143 A | 8/1993 | Dragon |
| 5,240,199 A | 8/1993 | Peters |
| 5,248,301 A | 9/1993 | Koenig et al. |
| 5,256,152 A | 10/1993 | Marks |
| 5,257,980 A | 11/1993 | Van Antwerp et al. |
| 5,265,822 A | 11/1993 | Shober, Jr. et al. |
| 5,269,799 A | 12/1993 | Daniel |
| 5,279,579 A | 1/1994 | D'Amico |
| 5,279,591 A | 1/1994 | Simon |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,350,392 A | 9/1994 | Purcell et al. |
| 5,376,082 A | 12/1994 | Phelps |
| 5,384,174 A * | 1/1995 | Ward et al. ................ 428/41.5 |
| 5,388,931 A | 2/1995 | Carlson |
| 5,391,151 A | 2/1995 | Wilmot |
| 5,403,288 A | 4/1995 | Stanners |
| 5,405,332 A | 4/1995 | Opalek |
| 5,429,613 A | 7/1995 | D'Amico |
| 5,449,349 A | 9/1995 | Sallee et al. |
| 5,487,506 A * | 1/1996 | Drummond et al. ........ 229/202 |
| 5,490,841 A | 2/1996 | Landis |
| 5,494,215 A * | 2/1996 | Drummond et al. ........ 229/202 |
| 5,505,709 A | 4/1996 | Funderburk et al. |
| 5,507,730 A | 4/1996 | Haber et al. |
| 5,519,167 A | 5/1996 | Kunimoto et al. |
| 5,520,654 A | 5/1996 | Wahlberg |
| 5,522,803 A | 6/1996 | Teisson-Simony |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,554,130 A | 9/1996 | McDonald et al. |
| 5,562,636 A | 10/1996 | Utterberg |
| 5,584,813 A | 12/1996 | Livingston et al. |
| 5,591,188 A | 1/1997 | Waisman |
| 5,599,315 A | 2/1997 | McPhee |
| 5,599,318 A | 2/1997 | Sweeney et al. |
| 5,643,220 A | 7/1997 | Cosme |
| 5,662,617 A | 9/1997 | Odell et al. |
| 5,665,071 A | 9/1997 | Wyrick |
| 5,665,075 A | 9/1997 | Gyure et al. |
| 5,681,323 A | 10/1997 | Arick |
| 5,695,476 A | 12/1997 | Harris |
| 5,704,920 A | 1/1998 | Gyure |
| 5,714,225 A | 2/1998 | Hansen et al. ............... 428/114 |
| 5,741,288 A | 4/1998 | Rife |
| 5,752,923 A | 5/1998 | Terwilliger |
| 5,810,835 A | 9/1998 | Ryan et al. |
| D402,538 S | 12/1998 | Wagter et al. |
| 5,851,197 A | 12/1998 | Marano et al. |
| 5,865,806 A | 2/1999 | Howell |
| 5,873,540 A | 2/1999 | Hardin |
| 5,899,886 A | 5/1999 | Cosme |
| 5,915,640 A | 6/1999 | Wagter et al. |
| 5,925,032 A | 7/1999 | Clements |
| 5,947,935 A | 9/1999 | Rinehart et al. |
| 5,951,523 A | 9/1999 | Osterlind et al. |
| 5,957,892 A | 9/1999 | Thorne |
| 5,968,011 A | 10/1999 | Larsen et al. |
| 5,975,120 A | 11/1999 | Novosel |
| 5,980,488 A | 11/1999 | Thorne |
| 5,984,224 A | 11/1999 | Yang |
| 5,984,897 A | 11/1999 | Peterson et al. |
| 5,992,787 A | 11/1999 | Burke |
| 6,017,328 A | 1/2000 | Fischell et al. |
| 6,039,629 A | 3/2000 | Mitchell ...................... 450/57 |
| 6,045,533 A | 4/2000 | Kriesel et al. |
| 6,056,718 A | 5/2000 | Funderburk et al. |
| 6,086,008 A | 7/2000 | Gray et al. |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stardella |
| 6,105,218 A | 8/2000 | Reekie |
| 6,120,482 A | 9/2000 | Szabo |
| 6,123,690 A | 9/2000 | Mejslov |
| 6,132,755 A | 10/2000 | Eicher et al. |
| 6,165,156 A * | 12/2000 | Cesarczyk et al. .......... 604/180 |
| 6,219,574 B1 | 4/2001 | Cormier et al. |
| 6,248,093 B1 | 6/2001 | Moberg |
| 6,293,925 B1 | 9/2001 | Safabash et al. |
| 6,302,866 B1 | 10/2001 | Marggi |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,379,335 B1 | 4/2002 | Rigon et al. |
| D456,692 S | 5/2002 | Epstein |
| 6,387,076 B1 | 5/2002 | Landuyt |
| 6,488,663 B1 | 12/2002 | Steg |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,575,475 B1 * | 6/2003 | Duncan ...................... 277/607 |
| 6,579,267 B1 | 6/2003 | Lynch et al. |

| | | | | | | |
|---|---|---|---|---|---|---|
| 6,588,454 B1* | 7/2003 | Johnson et al. ............... 138/90 | | 2004/0158207 A1 | 8/2004 | Hunn et al. |
| 6,595,962 B1 | 7/2003 | Perthu | | 2004/0171989 A1 | 9/2004 | Horner et al. |
| 6,607,509 B1 | 8/2003 | Bobroff et al. | | 2004/0178098 A1 | 9/2004 | Swenson et al. |
| 6,607,511 B1 | 8/2003 | Bobroff et al. | | 2004/0186446 A1 | 9/2004 | Ohshima |
| 6,629,949 B1 | 10/2003 | Douglas | | 2004/0204687 A1 | 10/2004 | Mogensen et al. |
| 6,726,649 B1 | 4/2004 | Swenson et al. | | 2004/0220528 A1 | 11/2004 | Garcia, Jr. |
| 6,811,545 B1 | 11/2004 | Vaillancourt | | 2004/0238392 A1 | 12/2004 | Peterson et al. |
| 6,814,720 B1* | 11/2004 | Olsen et al. ................ 604/339 | | 2004/0254433 A1 | 12/2004 | Bandis et al. |
| 6,824,530 B1 | 11/2004 | Wagner et al. | | 2004/0260235 A1 | 12/2004 | Douglas |
| 6,824,531 B1 | 11/2004 | Zecha, Jr. et al. | | 2004/0260250 A1 | 12/2004 | Harris et al. |
| 6,830,562 B1 | 12/2004 | Mogensen et al. | | | | |
| 2001/0004970 A1 | 6/2001 | Hollister et al. | | | | |
| 2001/0021827 A1 | 9/2001 | Ferguson et al. | | | | |

FOREIGN PATENT DOCUMENTS

| | | |
|---|---|---|
| DE | 101 06 074 A1 | 6/2002 |
| DK | 37 15 965 A | 1/1988 |
| EP | 0 239 244 B1 | 2/1987 |
| EP | 0 633 039 | 7/1994 |
| EP | 744 183 A2 | 11/1996 |
| EP | 0 916 361 A1 | 5/1999 |
| EP | 0 931 560 A1 | 7/1999 |
| EP | 1 060 757 A1 | 12/2000 |
| EP | 1 086 718 A | 3/2001 |
| EP | 0 775 501 | 6/2002 |
| FR | 2725902 | 10/1994 |
| GB | 478803 | 1/1938 |
| GB | 1 403 034 | 8/1975 |
| JP | 9217584 A | 9/1997 |
| JP | 2002-028246 | 1/2002 |
| WO | WO 87/06474 | 11/1987 |
| WO | WO 93/03787 | 3/1993 |
| WO | WO 93/05840 | 4/1993 |
| WO | WO 95/28327 A | 10/1995 |
| WO | WO 96/35472 A1 | 11/1996 |
| WO | WO 98/58693 | 12/1998 |
| WO | WO 99/33504 | 7/1999 |
| WO | WO 99/36009 | 7/1999 |
| WO | WO 99/56802 | 11/1999 |
| WO | WO 00/02614 | 1/2000 |
| WO | WO 00/03757 | 1/2000 |
| WO | WO 00/44324 A1 | 8/2000 |
| WO | WO 01/68180 | 9/2001 |
| WO | WO 02/46080 | 6/2002 |
| WO | WO 02/094352 | 11/2002 |
| WO | WO 02/100457 | 12/2002 |
| WO | WO 02/068014 | 1/2003 |
| WO | WO 03/015860 A1 | 2/2003 |
| WO | WO 03/026728 | 4/2003 |
| WO | WO 04/030726 A | 4/2004 |

Additional US references:

| | | |
|---|---|---|
| 2001/0039401 A1 | 11/2001 | Ferguson et al. |
| 2002/0068904 A1 | 6/2002 | Pluth et al. |
| 2002/0072720 A1 | 6/2002 | Hague et al. |
| 2002/0111581 A1 | 8/2002 | Sasso |
| 2002/0145073 A1 | 10/2002 | Swanson |
| 2002/0156427 A1 | 10/2002 | Suzuki et al. |
| 2002/0161332 A1 | 10/2002 | Ramey |
| 2002/0169419 A1 | 11/2002 | Steg |
| 2002/0183688 A1 | 12/2002 | Lastovich et al. |
| 2002/0193744 A1 | 12/2002 | Alesi et al. |
| 2003/0069548 A1 | 4/2003 | Connelly et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Satabash et al. |
| 2003/0176843 A1 | 9/2003 | Wilkinson |
| 2003/0181863 A1 | 9/2003 | Davis et al. |
| 2003/0181868 A1 | 9/2003 | Swenson |
| 2003/0181873 A1 | 9/2003 | Swenson |
| 2003/0187394 A1 | 10/2003 | Wilkinson et al. |
| 2003/0187395 A1 | 10/2003 | Wilkinson et al. |
| 2003/0199823 A1 | 10/2003 | Bobroff et al. |
| 2003/0225373 A1 | 12/2003 | Bobroff et al. |
| 2003/0225374 A1 | 12/2003 | Mathiasen |
| 2003/0229316 A1 | 12/2003 | Hwang et al. |
| 2004/0002682 A1 | 1/2004 | Kovelman et al. |
| 2004/0044306 A1 | 3/2004 | Lynch et al. |
| 2004/0049159 A1 | 3/2004 | Barrus et al. |
| 2004/0068231 A1 | 4/2004 | Blondeau |
| 2004/0087913 A1 | 5/2004 | Rogers et al. |
| 2004/0111068 A1 | 6/2004 | Swenson |
| 2004/0112781 A1 | 6/2004 | Hofverberg et al. |
| 2004/0138620 A1 | 7/2004 | Douglas et al. |
| 2004/0143218 A1 | 7/2004 | Das |
| 2004/0158202 A1 | 8/2004 | Jensen |

* cited by examiner

INFUSION DEVICE AND AN ADHESIVE SHEET MATERIAL AND A RELEASE LINER

FIELD OF THE INVENTION

The invention relates to an infusion device comprising a housing with an upper face plate and a lower face plate and a cannula connected to the lower face plate and through which a liquid is injected into the skin of a user; means for injecting the liquid and an adhesive sheet material placed in connection with the lower face plate and for securing the infusion device to the skin, said adhesive sheet material comprising a backing layer which has, on a portion of one surface, an adhesive layer, said adhesive layer being covered by a removable release liner, said sheet and release liner comprising a central aperture through which the cannula may act.

BACKGROUND

The invention also relates to an adhesive sheet material comprising a backing layer which has, on a portion of one surface, an adhesive layer, wherein the adhesive layer is covered by a removable release liner, said sheet and release liner comprising a central aperture.

Additionally, the invention relates to a release liner for covering an adhesive sheet material, said adhesive sheet material comprising a backing layer which has, on a portion of one surface, an adhesive layer, said adhesive layer being covered by the removable release liner International application No. PCT DK 02/00640, incorporated herein by the present reference, teaches an injection device for being located on the skin of a user, and from where eg insulin is injected via a cannula into the user, a subcutaneous infusion set being located on the skin by means of the injection device. The infusion device can be adhered to the skin by means of an adhesive pad that is connected to the lower face of the infusion device and, with its adhesive face, faces towards the skin of the user. Moreover, centrally of the pad/the adhesive sheet a recess will be provided corresponding to the cannula and a needle, located either here on upon activation emerging unimpededly. Upon penetration of the skin and subsequent activation of means in the injection device, injection is performed of the substance in question, which is preferably insulin.

BRIEF SUMMARY OF THE INVENTION

Prior to arrangement of the infusion device on the skin it is required that the release liner arranged on the adhesive face of the pad is removed. Typically, this is accomplished either by the release liner having several score lines for removing the release liner, or it is an option to remove it in one circular piece which is, however, difficult, without an ensuing risk of soiling the adhesive face and, likewise, it may be difficult to handle the injection device and hence there is a risk of losing the product.

Furthermore, an adhesive sheet is known from U.S. Pat. No. 5,384,174, that teaches a circular pad for being located on a user's skin, and wherein an adhesive face is arranged behind a release liner. The release liner is removed prior to application of the pad on the skin, as it typically comprises a pair of score lines in the release liner, such that the liner is removed in two, three pieces. There is consequently a risk that, during removal of this release liner, the user accidentally touches the adhesive face thereby transferring sebum particles to this, thereby reducing its ability to adhere to the skin. Likewise, the shape of the release liner is a contributing factor why it is difficult to handle, and therefore there is a risk of loosing it during handling of the pad.

It is thus the object of the present invention to remedy the above-identified problems and to provide a release liner or an adhesive material covered by a release liner and that can be used either alone or in combination with an infusion device, said release liner being removable in one piece as a strip, thereby reducing the risk of the user handling the product erroneously, and, likewise, little force is needed to remove the release liner since, other things being equal, all it takes is just to overcome the adhesive force of the piece of strip currently being removed by the user.

This object is obtained with an infusion device comprising a housing with an upper face plate and a lower face plate and a cannula connected to the lower face plate and through which a liquid is injected into the skin of a user; means for injecting the liquid, and an adhesive sheet material placed in connection with the lower face plate and for securing the infusion device to the skin; the adhesive sheet material comprising a backing layer which has, on a portion of one surface, an adhesive layer; said adhesive layer being covered by a removable release liner and wherein the release liner also comprises at least one score line, wherein the starting point for the score line for stripping it off the adhesive layer is placed in the periphery of the release liner and wherein the score line is an unbroken line that does not intersect itself and continues to an end point placed on the border of the periphery of the release liners central aperture.

This object is also achieved by an adhesive sheet comprising a backing layer which has, on a portion of one surface, an adhesive layer, said adhesive layer being covered by a removable release liner said sheet and release liner comprising a central aperture and wherein the release liner also comprises at least one score line, wherein the starting point for the score line for stripping it off the adhesive layer is placed in the periphery of the release liner, and wherein the score line is an unbroken line that does not intersect itself and continues to an end point placed on the border of the periphery of the release liner's central aperture.

This object is also achieved by a release liner for covering an adhesive sheet material, wherein said adhesive sheet material comprises a backing layer which has, on a portion of one surface, an adhesive layer, said adhesive layer being covered by the removable release liner and wherein the release liner also comprises at least one score line, wherein the starting point for the score line for stripping it off the adhesive layer is placed in the periphery of the release liner, and wherein the score line is an unbroken line that does not intersect itself and continues to an end point placed on the border of the periphery of the release liner's central aperture.

Thus the invention works in that, once the pad or an adhesive substance covered by a release liner is located on the infusion device, the user seizes the injection device and with the adhesive face facing towards him, he seizes a portion of the release liner, where a starting area will primarily be a tab. The tab will be situated outside the delimitation of the pad as such or the glue and it is used as starting point for stripping off the release liner in one piece. The shape of the adhesive sheet is preferably circular. The sheet may also be configured with other shapes, including oval, triangular, rectangular, etc., and wherein the scoring is performed helically so as to take its starting point in the periphery of the release liner and coil inwardly in a single helix, where it ends at a central opening where the cannula either protrudes or will be caused to protrude upon activation.

As mentioned, by a pull the release paper can be removed in one single narrow strip and this is why only little force is needed to remove it and, likewise, the handling is easy. The handling will take place in the same manner as in case the adhesive sheet were used without an injection device, eg as an ordinary band aid. It is thus a crucial point that the scoring that takes place brings about a strip and that the score line thus generated does not at any point intersect itself as this would result in a number of separate sheet papers.

Now, the injector device is subsequently activated, whereby the infusion device is located on the user's skin and, via the adhesive face, its contact therewith is hereby ensured; for further reference see also international application No. PCT/DK 02/00640.

By providing an infusion device where the adhesive sheet and release liner are substantially circular and an adhesive sheet material where the adhesive sheet and the release liner are substantially circular and a release liner where the release liner is substantially circular, a much used shape of the adhesive sheet and the release liner is obtained.

By providing an infusion device according to the invention further including a score line comprising a spiral or helix and an adhesive sheet according to the invention further including a score line comprising a spiral or helix and a release liner according to the invention further including a score line comprising a spiral or helix, a convenient shape of the score line is accomplished since a helical scoring brings about a simple and reproducible strip; albeit it is an option that the helical score line thus provided could bend and assume such course that the distance from the sheet periphery to the score line was not continuously decreasing, but rather decreasing, increasing, decreasing, and so on.

By providing an infusion device according to the invention 4, where the release liner comprises a tab for gripping the release liner and starts the stripping from the starting point and an adhesive sheet according to the invention where the release liner comprises a tab for gripping the release liner and starts the stripping form the starting point and a release liner according to the invention, where the release liner comprises a tab for gripping the release liner and starts the stripping from the starting point a good starting area is obtained for stripping off the release liner.

The invention will now be explained in further detail with reference to the drawing, wherein.

Figure 6:
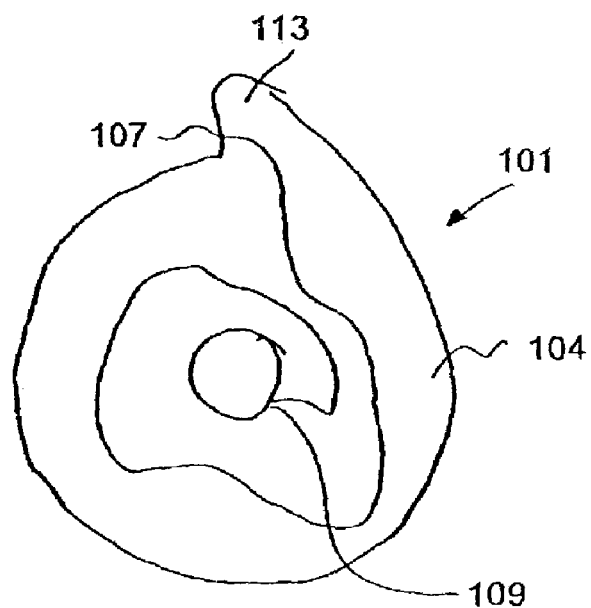
FIG. 6 shows an adhesive sheet material shaped to be essentially circular and having an applied release liner comprising a score line that is an unbroken line that extends curved and in a helix that coils towards the centre to the central opening.
Figure 7:
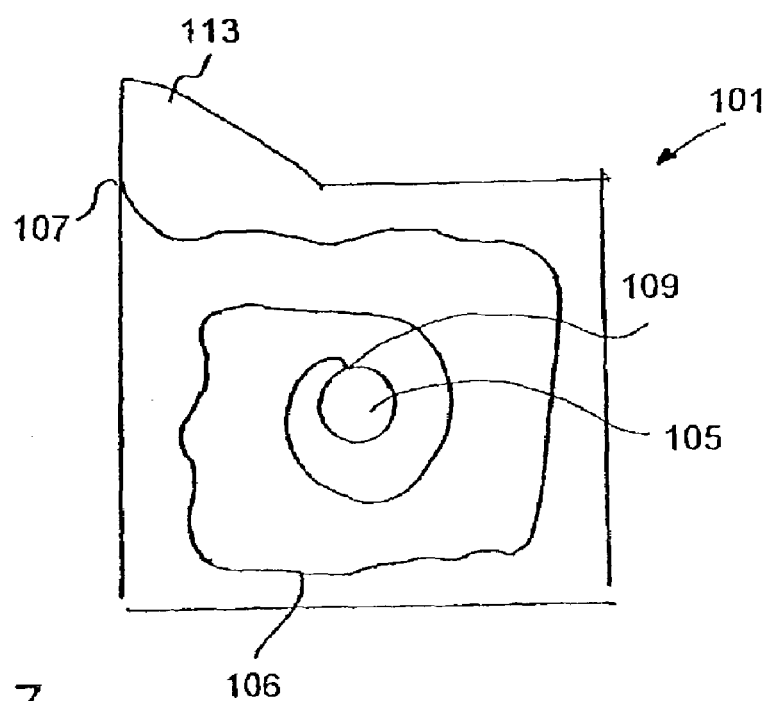

in principle FIG. 7 shows the same as FIG. 6, but wherein the design is a rectangular sheet material.

DETAILED DESCRIPTION OF THE PREFERRED EMBODIMENTS

Figure 1:
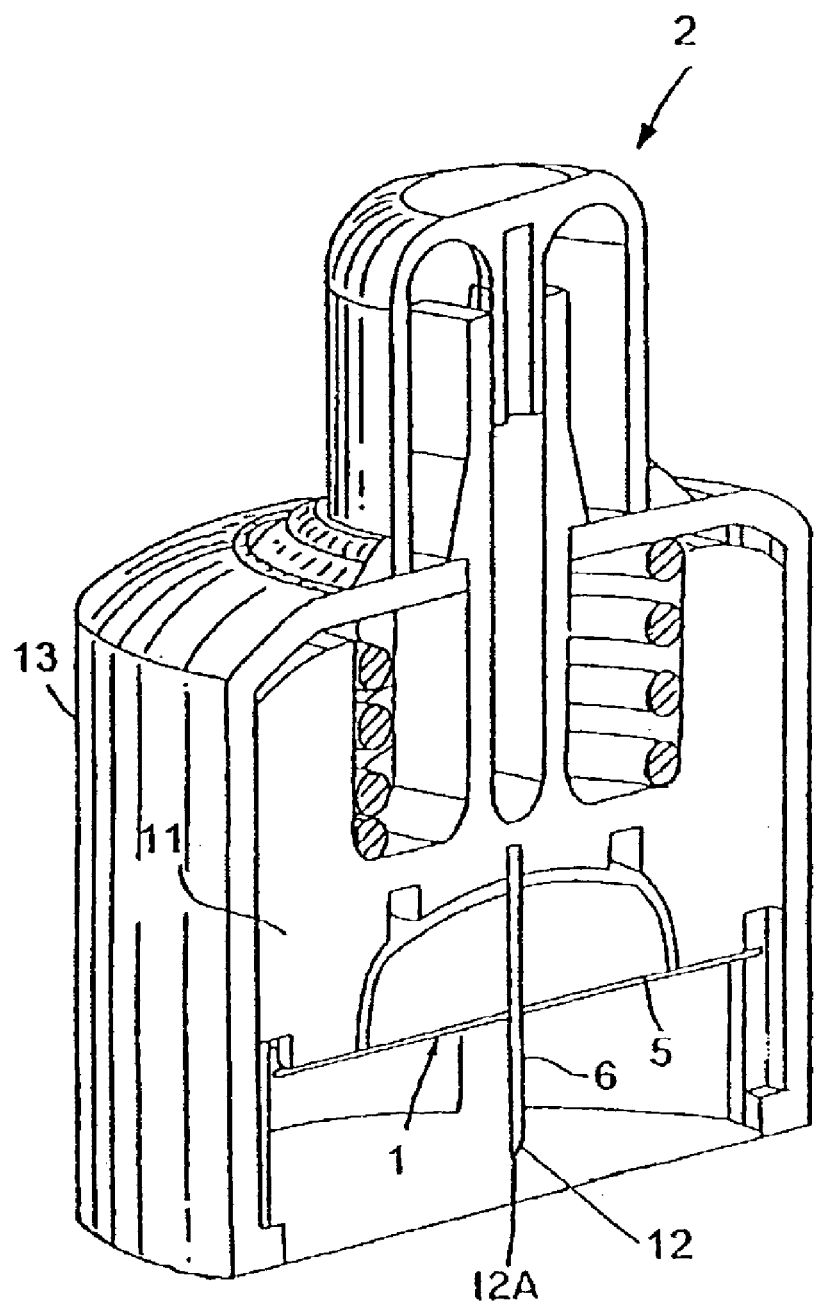
FIG. 1 shows an injection device in a sectional view and as known from international application No. PCT/DK02/00640, on which an adhesive sheet is arranged and comprising a release liner according to the invention.

An injector device shown schematically in FIG. 1 by the reference numeral 2 is provided for quick and easy placement of a subcutaneous infusion set 1, and may then be discarded safely. The infusion set 1 with a cannula 6 extending there from is shown schematically only.

The injector device 2 includes a plunger 11 having thereon a medical insertion needle 12 with a pointed end 12A. The plunger 11 is arranged for longitudinal sliding movement within a device housing 13 between a forward advanced position and a rearward retracted position. The device housing 13 may have a circular, square or any desired cross-sectional shape. The device housing 13 and the plunger 11 are preferably formed of a plastics material in a moulding process.

The infusion set 1 is used to infuse medical fluids such as insulin to a patient, and generally includes a housing with an internal chamber (not shown) that receives medication via infusion tubing. An enlarged base of the infusion set 1, also designated a lower face plate 5, is provided on the housing for stable affixation thereof to the skin of the patient. The enlarged base 5 carries an adhesive and is provided with a release sheet or removable release liner 104 which is removed to expose the adhesive prior to placement of the infusion set. Alternatively, the base 5 may be sized to allow the infusion device to be fixed to the patient by an adhesive patch. The infusion set has a protruding soft and flexible cannula 6, which communicates with the internal chamber, and a passage sealed by a sealing membrane extends through the housing opposite the cannula 6. The medical insertion needle 12 of the injector device 2 extends through the passage, into the internal chamber and through the cannula 6, when the infusion set 1 is mounted in position on the injector device After transcutaneous placement of the cannula 6, the injector device 2 with the insertion needle 12 is retracted from the infusion set 1 to permit medication delivery through the cannula 6 to the patient.

Figure 2:
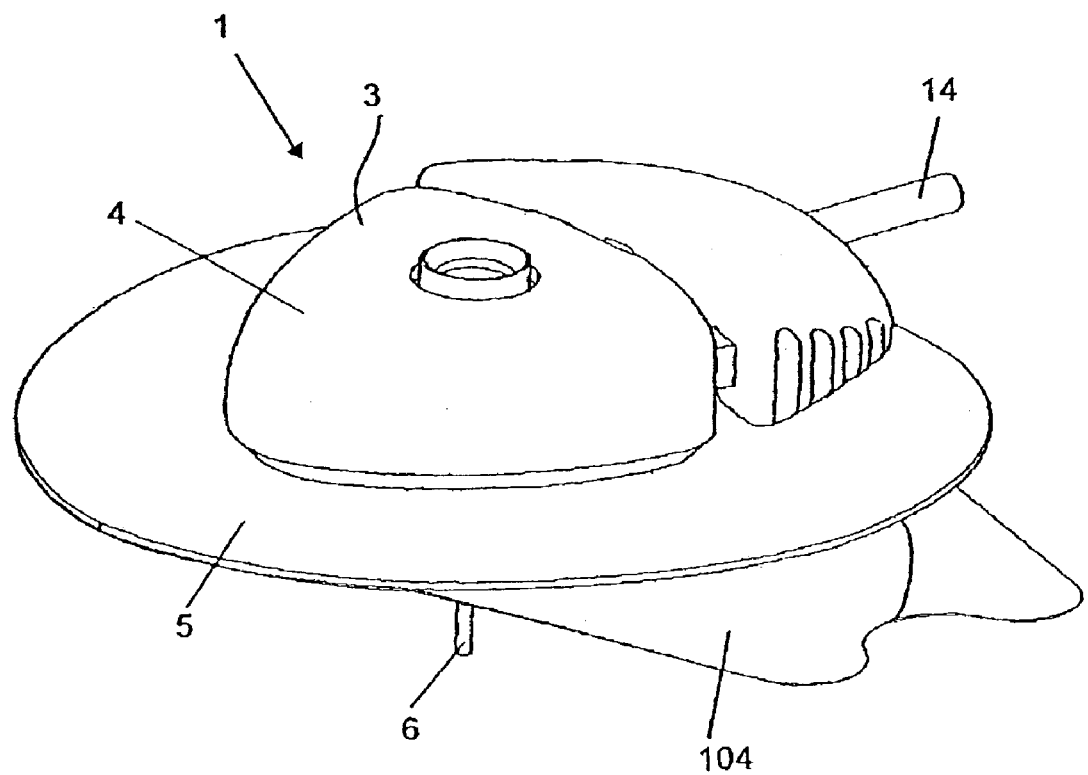
FIG. 2 shows an infusion device suitable for use with an injector device disclosed in FIG. 1.

FIG. 2 shows an example of an infusion set 1 suitable for use with an injector device. The infusion set 1 includes a housing 3 with an internal chamber (not shown). The internal chamber receives medication via infusion tubing 14 which may be detachably connected to the housing 3 by any suitable connector. The medication is delivered by means for injecting the liquid for instance a pump or syringe. The base 5 of the housing 3 and opposite the upper face, plate 4 may carry an adhesive and be provided with a release sheet 104 which is removed to expose the adhesive prior to placement of the infusion set. The infusion set 1 has a protruding soft and flexible cannula 6, which communicates with the internal chamber. An internal passage which is sealed by a sealing membrane and which is penetrated by the insertion needle of the injector device extends through the housing opposite the cannula 6.

Figure 3A:
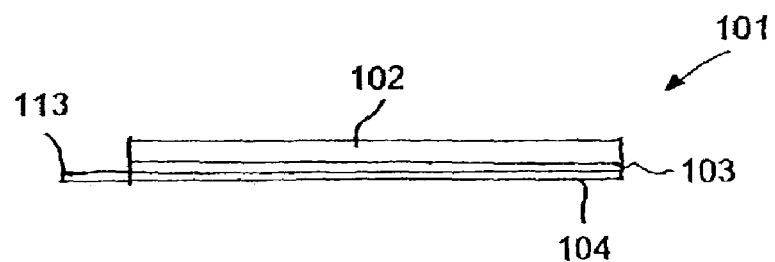
FIG. 3a shows adhesive sheet material, in a side view.

FIG. 3a shows an adhesive sheet material 101 that is suitable for being arranged on the lower face plate 5 shown in FIG. 2. The adhesive sheet material 101 comprises a backing layer 102 that can be manufactured from polyester fibre and on the one face of which an adhesive layer 103 is applied that is conveniently covered with a release liner 104, said release liner being a non-adhesive paper, which distinguishes itself in that, following removal thereof from adhesive layer, the adhesive remains on the backing layer, and, likewise, no residue of the adhesive substance remains on the release liner as such.

Figure 3B:
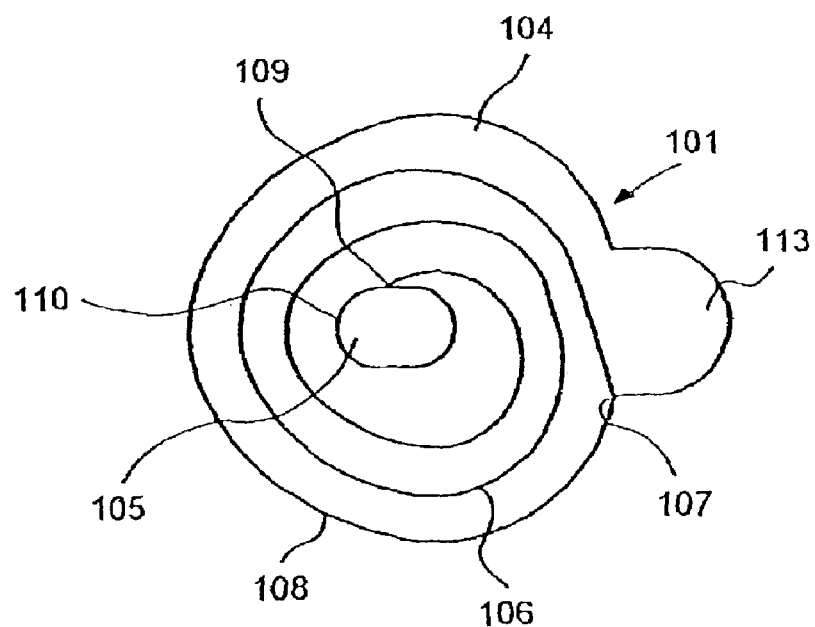
FIG. 3b shows an adhesive sheet material, seen from the bottom, and wherein the release liner with helical score line applied.

FIG. 3b shows a preferred embodiment comprising an essentially circular sheet material, at the centre of which a central aperture 105 is provided that can be configured to be oval, circular, triangular and in which, in connection with an infusion device, provides space for the cannula This aperture is delimited by a border line 110. The outer delimitation of the removable release liner is referred to as the periphery 108. Optionally, this periphery may comprise a tab 113, which is preferably constituted exclusively by the release liner and will thus serve as starting area for stripping off the release liner. In the periphery 108 of the release liner is a starting point 107 for the score line 106, said score line 106 extending helically and in an unbroken line towards the centre of the release liner and ending in the edge of the central aperture 105 in an end point 109. Thus, if the tag/tab 113 is seized, it will require only little force to remove the liner from the subjacent adhesive layer, and the release liner can be stripped off in one single strip, leaving the adhesive face 103 exposed.

Figure 4:
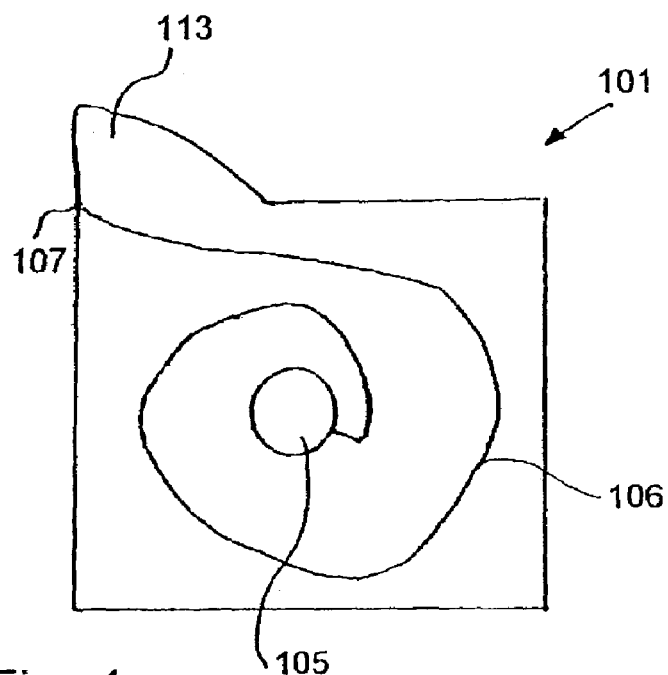
FIG. 4 shows a rectangular adhesive sheet material with a helical score line for providing a removable release liner.

FIG. 4 shows an example of a rectangular sheet material and a rectangular release liner, and wherein a score line 106 is provided that also extends helically and with a starting point 107 peripherally of the adhesive sheet material and ending at the centre where the central aperture 105 is provided.

Figure 5:
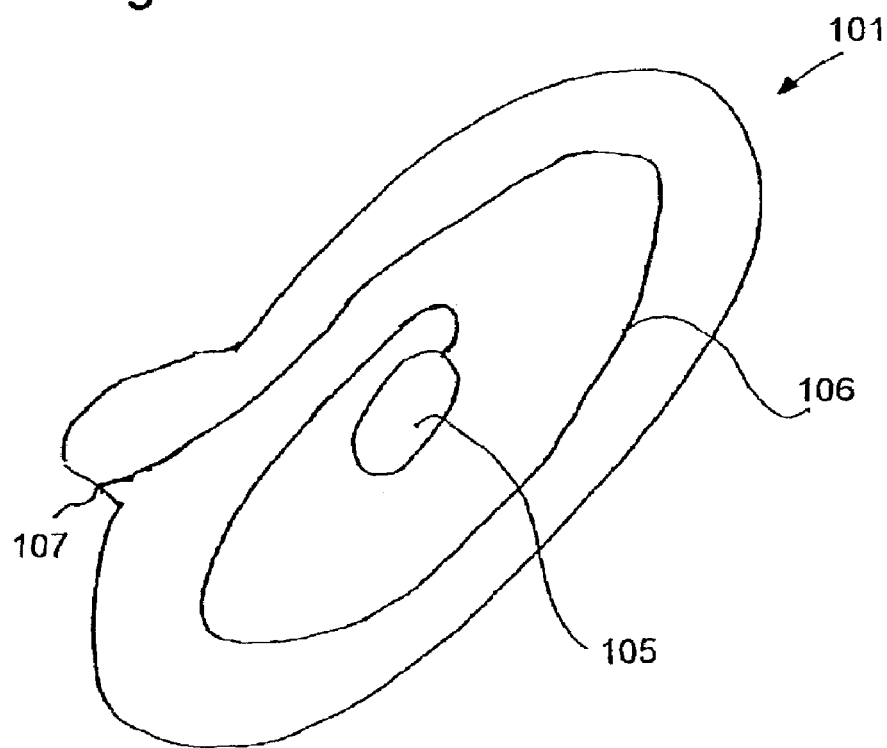
FIG. 5 shows an oval adhesive sheet material with a helical score line for providing a removable release liner.

FIG. 5 shows a corresponding system wherein the pad with release liner has an oval shape.

FIG. 6 shows essentially the same as FIG. 3b, but wherein the score line 106 does not have an evenly decreasing distance to the outer periphery 108, but rather extends in a curved manner such that the distance to the outer periphery 108 increases/decreases/increases, and wherein the essential aspect is that the score line 106 does not at any point intersect itself, since this would mean that the removable release liner 104 cannot be removed in one piece as it is one of the objects of the present invention.

Finally in principle FIG. 7 shows the same as FIG. 4, but wherein a more curved course is provided and wherein the score line is not shaped circularly, but has a rather rectangular course.

The invention claimed is:

1. An infusion device (1) comprising a housing (3) with an upper face plate (4) and a lower face plate (5) and a cannula (6) connected to the lower face plate (5) and through which a liquid is injected into the skin of a user; means for injecting the liquid, and an adhesive sheet material (101) placed in connection with the lower face plate (5) and for securing the infusion device (1) to the skin; said adhesive sheet material (101) comprising a backing layer (102) which has, on a portion of one surface, an adhesive layer (103); said adhesive layer (103) being covered by a removable release liner (104), said sheet and release liner (104) comprising a central aperture (105) through which the cannula (6) may act, characterized in that the release liner (104) comprises at least one score line (106) comprising a spiral or helix, that the starting point (107) for the score line (106) for stripping the release liner off of the adhesive layer (103) is placed in the periphery (108) of the release liner (104), and that the score line (106) is an unbroken line that does not intersect itself and continues to an end point (109) placed on the border of the periphery (110) of the release liners central aperture (105).

2. An infusion device (1) according to claim 1, characterized in that the adhesive sheet (101) and release liner (104) are substantially circular.

3. An infusion device (1) according to claim 2, characterized in that the release liner (104) comprises a tab (113) for gripping the release liner (104) and starts the stripping from the starting point (107).

4. An adhesive sheet material (101) comprising a backing layer (102) which has, on a portion of one surface, an adhesive layer (103), said adhesive layer (103) being covered by a removable release liner (104), said sheet and release liner (104) comprising a central aperture (105), characterized in that the release liner (104) also comprises at least one score line (106) comprising a spiral or helix, that the starting point (107) for the score line (106) for stripping the release liner off the adhesive layer (103) is placed in the periphery (108) of the release liner (104), and that the score line (106) is an unbroken line that does not intersect itself and continues to an end point placed on the border of the periphery (110) of the release liner's central aperture (105).

5. An adhesive sheet material (101) according to claim 4, characterized in that the adhesive (101) sheet and the release liner (104) are substantially circular.

6. An adhesive sheet material (101) according to claim 5, characterized in that the release liner (104) comprises a tab (113) for gripping the release liner (104) and starts the stripping from the starting point (107).

7. A release liner (104) for covering an adhesive sheet material (101), wherein said adhesive sheet material (101) comprises a backing layer (102) which has, on a portion of one surface, an adhesive layer (103), said adhesive layer (103) being covered by the removable release liner (104), characterized in that the release liner (104) comprises a central aperture and at least one score line (106) comprising a spiral or helix, that the starting point (107) for the score line (106) for stripping the release liner off the adhesive layer (103) is placed in the periphery (108) of the release liner (104), and that the score line (106) is an unbroken line that does not intersect itself and continues to an end point placed on the border of the periphery (110) of the release liner's central aperture (105).

8. A release liner (104) according to claim 7, characterized in that the release liner (104) is substantially circular.

9. A release liner according to claim 8, characterized in that the release liner (104) comprises a tab (113) for gripping the release liner (104) and starts the stripping from the starting point (107).

10. The infusion device according to claim 1 wherein the release liner comprises a tab for gripping the release liner and starts the stripping from the starting point.

11. The adhesive sheet material according to claim 4, wherein the release liner comprises a tab for gripping the release liner and starts the stripping from the starting point.

12. The release liner according to claim 7, wherein the release liner comprises a tab for gripping the release liner and starts the stripping from the starting point.

* * * * *